United States Patent [19]

Meehan

[11] Patent Number: 4,633,533
[45] Date of Patent: Jan. 6, 1987

[54] METHOD AND ARTICLE FOR NEUTRALIZING OFFENSIVE ODORS

[76] Inventor: Frank Meehan, 203 Cathedral Ave., Hempstead, N.Y. 11550

[21] Appl. No.: 825,318

[22] Filed: Feb. 3, 1986

Related U.S. Application Data

[63] Continuation-in-part of Ser. No. 608,185, May 8, 1984, Pat. No. 4,567,613.

[51] Int. Cl.4 .............................................. E03D 9/02
[52] U.S. Cl. ......................................................... 4/222
[58] Field of Search .................... 4/222, 223; 222/108, 222/212, 111, 215, 183, 206

[56] References Cited

U.S. PATENT DOCUMENTS

| | | | |
|---|---|---|---|
| 570,518 | 11/1896 | Taussig | 4/222 |
| 2,438,906 | 4/1948 | Elsas et al. | 222/108 |
| 3,474,936 | 10/1969 | McDonnell | 222/212 X |
| 3,628,697 | 12/1971 | Dowson | 222/111 |
| 3,724,722 | 4/1973 | Ballo | 222/215 X |
| 3,850,346 | 11/1974 | Richardson et al. | 222/215 X |
| 4,324,348 | 4/1982 | Johnson et al. | 222/183 X |
| 4,446,991 | 5/1984 | Thompson | 222/183 X |
| 4,457,455 | 7/1984 | Meshberg | 222/183 X |
| 4,531,655 | 7/1985 | Putman | 222/183 X |
| 4,531,656 | 7/1985 | Nitchman et al. | 222/183 X |

Primary Examiner—Henry K. Artis
Attorney, Agent, or Firm—Roberts, Spiecens & Cohen

[57] ABSTRACT

A method and apparatus for neutralizing odor of human evacuation into a toilet facility by dispensing a deodorant liquid dropwise into the toilet facility comprising storing an odor-neutralizing liquid in an inner container and supporting the inner container in an outer container. An outlet is provided in the inner container which opens externally of the outer container and the outlet is formed so that by application of external force on the inner container the odor-neutralizing liquid can be discharged dropwise when the inner container is held in an inverted position and the outlet faces downwardly. The drops of the odor-neutralizing liquid are deposited into the toilet facility prior to use thereof.

19 Claims, 14 Drawing Figures

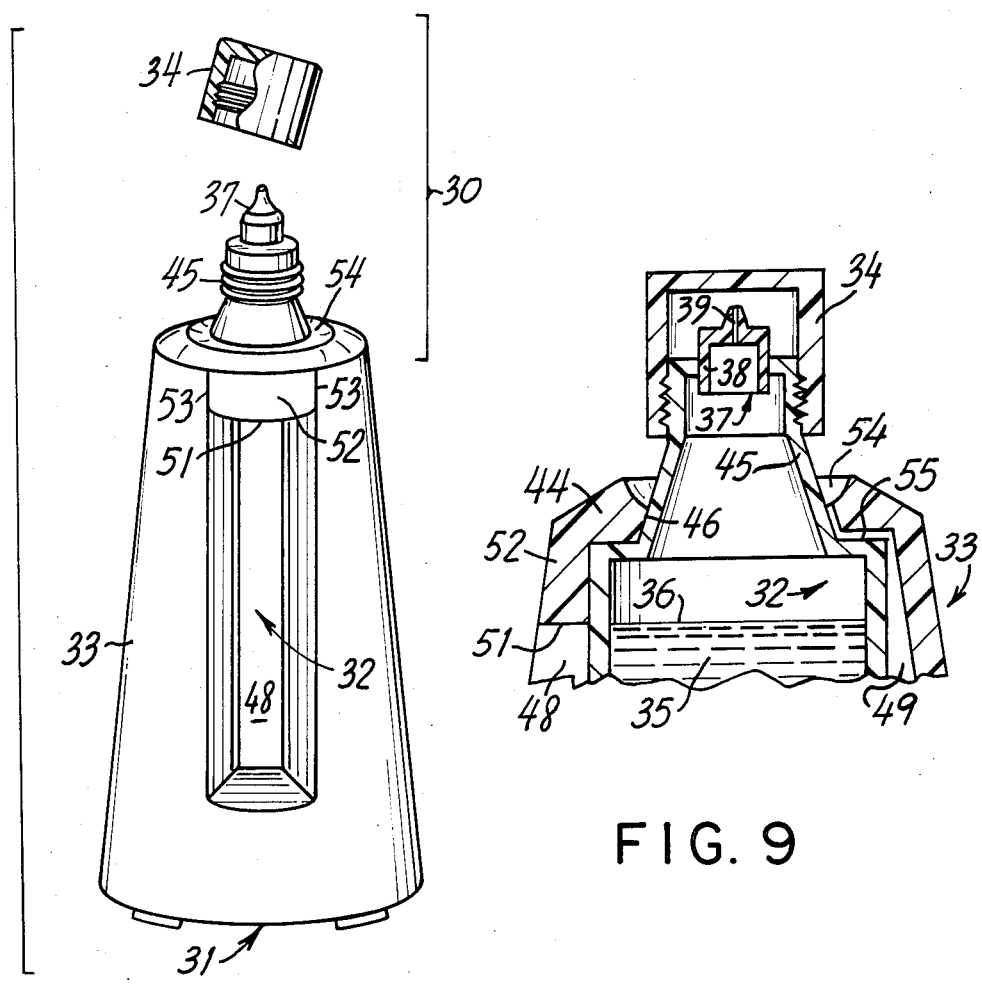
FIG. 8
FIG. 9
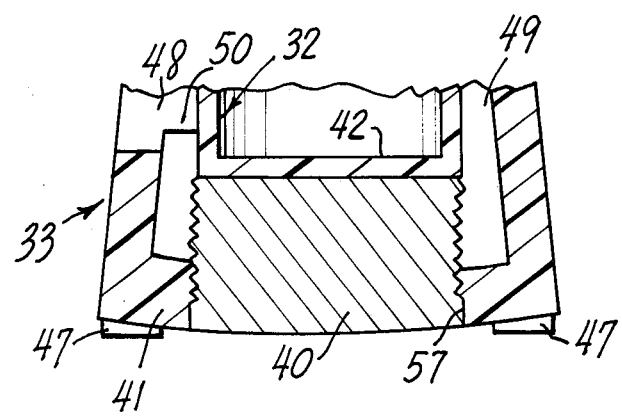
FIG. 10

METHOD AND ARTICLE FOR NEUTRALIZING OFFENSIVE ODORS

CROSS RELATED APPLICATION

This application is a Continuation-In-Part of Application Ser. No. 608,185, filed May 8, 1984 and issued as U.S. Pat. No. 4,567,613.

FIELD OF THE INVENTION

The invention relates to a throwaway article and associated method for neutralizing offensive odors, particularly those produced by fecal matter.

The invention also relates to a method and means for dispersing liquid deodorant dropwise for neutralizing offensive odors.

The invention has particular applicability for use in toilets and, particularly, where disposal may not be immediate, such as bedpans and portable toilets and on small boats, busses, and the like.

The invention also has special applicability to use in small quarters with poor ventilation.

SUMMARY OF THE INVENTION

Despite the wellknown features in the body of art disclosed hereinabove, there is need for the use of an article which can be readily stored and employed in use before generation of an odor in order to counteract the odor.

An important deficiency in the known art is the absence of an article which is capable of use both in the presence or absence of water.

An object of the invention is to provide an inexpensive package and associated method which will overcome the disadvantages of the known art and enable use in toilet facilities with or without water.

A further object of the invention is to provide a throwaway package which is relatively inexpensive and which is capable of being carried for activation at the time of use.

Yet another object of the invention is to provide a throwaway package which will allow itself to be activated without contaminating either the user or his or her surroundings.

Still another object of the invention is to provide a throwaway article of the above character which employs a minimal quantity of active substance and which is readily disposable and is biodegradable.

Still another object of the invention is to provide a throwaway article of the above character which is openable by peeling and which is introduced into the toilet facility prior to use and is thereafter flushed away, leaving no scent behind.

In accordance with the above, and further objects of the invention, there is provided a throwaway particle for neutralizing offensive odors which comprises a sheet of foldable material having a fold-line dividing the sheet to first and second portions, at least one of which includes a grid region therein on which an odor neutralizing liquid is adsorbed. The sheet is folded about the fold line to bring the first and second portions in confronting relation so that the article is ready for use. The sheet of foldable material is impervious to the odor-neutralizing liquid to prevent leakage thereof through the material and dissipation of any odor thereof.

The seal of the sheet is peelable to permit the user to open the package and expose the odor neutralizing liquid adsorbed in the grid region.

The fold line joining the first and second portions of the sheet applies a slight bias to the first and second portions to oppose complete unfolding of the portions into a flat state so that the unfolded sheet will have a slight V-shaped configuration. Thereby, if the unfolded sheet is deposited face down on a flat surface the grid region with adsorbed liquid will be disposed above the flat surface and thereby capable of releasing the odor neutralizing liquid to the ambient atmosphere.

In accordance with a feature of the invention, preferably the sheet of foldable material is biodegradable such as gelatin.

In accordance with a further feature of the invention, the odor neutralizing liquid is contained in a petroleum base which is lighter than water and highly dispersable therein so that the liquid will be broken into a multitude of droplets which will be dispersed on the surface of the water.

An essential aspect of the invention is that the package and its associated method of use does not contemplate after usage in the manner of conventional coverup sparys and leave a residual odor which in many cases, itself is offensive but, rather, is readied for use by the simple act of opening the package and depositing the same into the toilet facility after which it is removed along with the offensive material. The odor neutralizing liquid directly counteracts the offensive odor in a generally substantially confined environment.

Another object of the invention is to provide a method and article for dispensing a deodorant liquid dropwise into a toilet facility in order to counteract undesirable odor.

A further object of the invention is to provide such a method and article in which the deodorant liquid is stored in concentrated liquid form in an inner container such that the deodorant liquid is isolated from a supporting outer container.

Another object of the invention is to provide such a method and article in which any contact of the user with the deodorant liquid is minimized.

Another object of the invention is to provide such a method and article in which any spillage of liquid will be captured to prevent contact with the user.

In further accordance with the invention, the article for dispensing deodorant liquid dropwise comprises an inner container for the deodorant liquid, said liquid being floatable in water in dispersed droplet form, the inner container having outlet means for dispensing of the liquid therefrom. The inner container is supported within an outer container through which the liquid in the inner container is visible. The outer container has means by which actuating force can be applied to the inner container to cause discharge of liquid dropwise through the outlet means when the inner container is inverted and the outlet means faces downwardly.

In accordance with a feature of the invention, the means on the outer container by which actuating force can be applied to the inner container comprises an actuator element in the vicinity of an opening in the outer container through which the inner container is visible.

A further feature of the invention is the utilization of the separate inner container for the deodorant liquid which frees the outer container to be of substantial size to discourage portable carrying of the article within a pocket or purse. With this in mind, the invention further contemplates a weight within the outer container to hold the article in an upright position on a horizontal surface.

A further feature of the invention is to make the inner container replaceable in the outer container so that when the deodorant liquid is spent, the exhausted inner container can be removed and replaced with a fresh, filled inner container.

According to another feature of the invention, means are provided for capturing any overflow liquid from the outlet means of the inner container in order to prevent contact with the user.

The invention further contemplates a method of neutralizing odor from human evacuation into a toilet facility which comprises storing an odor neutralizing liquid in an inner container, in turn, supported in an outer container. The inner container has an outlet which opens externally of the outer container and the outlet is formed so that application of external force to the inner container will produce dropwise discharge of the odor neutralizing liquid when the inner container is held in an inverted position in which the outlet faces downwardly.

In order to neutralize undesired odor, the odor-neutralizing liquid is deposited dropwise into the toilet facility by application of external force to the inner container.

A feature of the method is that the external force is applied to the inner container by application of force to the outer container.

Another feature of the method of the invention, is to capture any overflow liquid from the outlet of the inner container in a reservoir in the outer container.

Still another feature of the method of the invention is to replace the inner container in the outer container with a fresh, filled, inner container after the liquid in the first inner container is spent.

Still another feature of the method of the invention is to show the amount of liquid content in the inner container through the outer container, preferably via a slot or opening therein.

BRIEF DESCRIPTION OF THE FIGURES OF THE DRAWING

FIG. 8 is a diagrammatic perspective view showing another embodiment of an article adapted for dispensing a deodorant liquid in which a cap of the article is separated therefrom and is shown partially broken away in section;

FIG. 9 is a sectional view of a top part of the article on enlarged scale;

FIG. 10 is a sectional view of a bottom part of the article on enlarged scale;

DETAILED DESCRIPTION OF THE PREFERRED EMBODIMENTS

Figure 2:
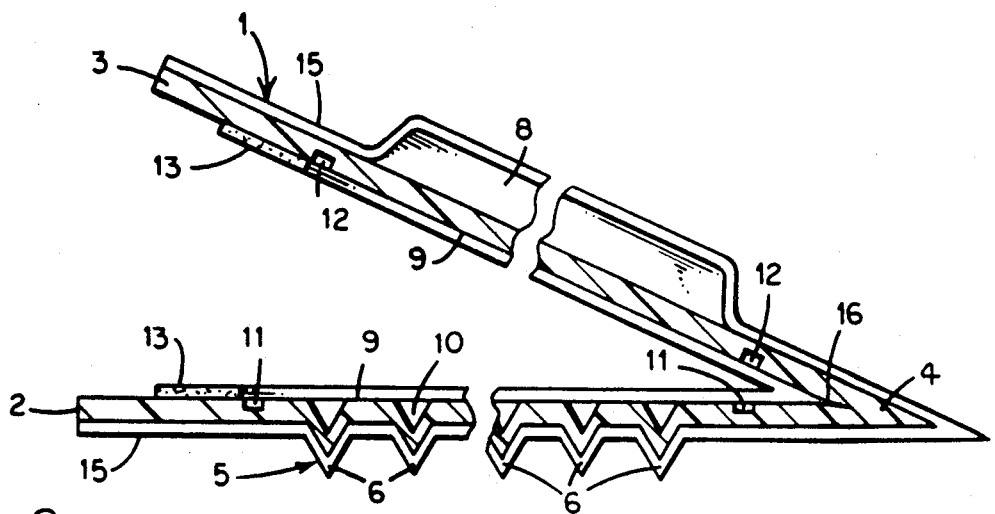
FIG. 2 is a sectional view taken along line II—II with the throwaway article partially folded towards the closed state.

In the drawing is illustrated a throwaway or disposable article 1 for neutralizing offensive odors. The article 1 comprises a sheet of material having portions 2 and 3 foldably joined at a fold line or hinge 4. The hinge 4 is formed by removing material at the join line of portions 2 and 3 so that the portions can be folded into confronting relation as shown in FIG. 2 where the article is in the partially folded state.

Portion 2 includes a grid region 5 composed of a series of parallel crenalations 6 adapted for adsorbing liquid, as will be explained more fully later. The portion 3 also includes a grid region 7 whose crenalations 8 extend in a direction perpendicular to crenalations 6.

When the portions 2 and 3 are folded into confronting relation, flat surfaces 9 of the portions in the grid regions 5 and 7 will come into confronting relation in order to substantially isolate the hollows 10 of the crenalations in which the liquid is contained. In this way, the adsorbed liquid will be divided up into multitudes of miniscule droplets which will be readily adsorbed in the hollows.

The crenalations in the grid regions 5 and 7 expand the surface area of the portions 2 and 3 of the sheet to break up the liquid droplet so that it can be adsorbed over the surface area as a non-flowable film in the confined region. As a consequence, when the article is opened, the liquid will not splatter on the user.

Under certain circumstances, it may be possible to utilize only one grid on one portion and instead of the illustrated construction of the grid formed by the crenalations, it may be possible to provide a surface treatment of the material such as by roughening the surface thereof to achieve the adsorbtion of the liquid.

Encircling the grid region 5 is a continuous groove 11, while surrounding the grid region 7 is a continuous groove 12. The grooves 11 and 12 isolate the grid regions 5 and 7 and the liquid therein from the remainder of the article for a purpose which will become evident hereafter.

Surrounding the grid regions in both portions 2 and 3 is an adhesive border 13. When the sheet is folded around hinge 4, the adhesive border seals itself by contact at both portions. It is noted that the grooves 11 and 12 isolate the adhesive border 13 in order to prevent any contact between the liquid in the grid regions and the adhesive. The grooves 11 and 12 also flank the hinge 4 to prevent any penetration of liquid to the hinge which could lead to splatter upon opening of the article.

When the article is closed and the adhesive border 13 has been brought into contact from both portions, the article is in readiness for use. A pair of bare tabs 14 are formed at the opposite ends to serve as an engagement means which will allow the user to open the article. The adhesive in the border 13 allows the article to be opened by application of separating pressure to the tabs 14.

The material of the article 1 can be of wide ranging composition provided that it is impermeable to the liquid which is adsorbed in the grid regions. Moreover, not only must it be impermeable to the liquid, it must also be impermeable to the deodorant smell thereof. A suitable material for the sheet of the article is PET film and it can have a thickness of the order of 0.003 to 0.010 inches. Different materials may have different thicknesses and the thickness can also vary as a function of the liquid which is adsorbed in the grid regions. There are numerous pressure-sensitive peelable adhesives for PET material currently available on the market, as will be wellknown to those skilled in the art and not requiring any elaboration herein.

According to a feature of the invention, the sheet material of the article 1 can advantageously be made of a hardened gelatin so that it will be biodegradable. The closure of the portions at the adherent border 13 can be made by forming a moisture or heat seal between the portions. Thereby, the portions become firmly joined together to form an airtight non-permeable seal which nevertheless is openable to gain access to the grid regions 5 and 7 in use. When the material of the article 1 is composed of gelatin, this is coated with a layer of biodegradable paper 15 to inhibit the exposure of the gelatin and minimize moisture degradation as well as inhibit heat transfer and consequent premature melting. Preferably, a taste offensive substance is placed into the coating to prevent ingestion by children and animals. The taste offensive substance can be a bitter flavoring material alum, peppers, a concentrate of sweetners, or the like. The taste offensive substance must also be non staining. If desired, the entire article 1 can be packed in its own cellophane packet.

The liquid which is adsorbed in the grid regions 5 and 7 is intended to serve the function of neutralizing offensive odors, particularly those produced by human fecal matter, and it is intended that the entire article 1 can be opened at the time of use to expose the adsorbed liquid in the grid regions to the ambient atmosphere prior to use of a toilet facility. The liquid comprises a potent volatile deodorant which is capable of nullifying offensive odors and various substances are adaptable for this purpose. By way of example, an applicable deodorant liquid is available under the trademark "SCENT-GO" manufactured by the Senoret Chemical Company of Kirkwood, Mo. The deodorant is based on petroleum distillates and ortho dichlorobenzene which is effective to keep the deodorant in floating state on water in highly dispersed droplet form. The deodorant liquid is air activated and molecularly interactive in the air to counteract offensive odors. As a consequence, the deodorant will be extremely effective when the article 1 is opened and dropped into a toilet bowl.

According to the conception of the invention, the article 1 is utilized prior to evacuation by opening the article and depositing it into the facility which is to be used. Generally, the product acts in a captive atmosphere and the deodorant is effective by molecular reaction to destroy the malodorous smell. When the toilet is flushed, the article 1 is removed and there is no lingering deodorant scent, as in the case of conventional sprays and slow-release liquids. Indeed, such scents themselves frequently are offensive to the users.

Figure 3:
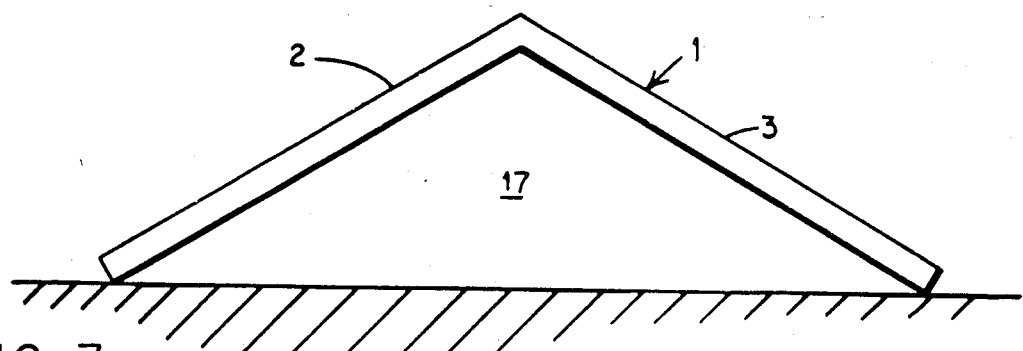
FIG. 3 is a diagrammatic illustration showing the article in unfolded ready to use state after it has been deposited on a flat surface.

Since it is also contemplated for the article 1 to be utilized under non-aqueous conditions, such as bedpans, it is important that the article when opened not be capable of being rendered ineffective such as by a smothering action on the adsorbed liquid in the grid regions. For this purpose, the hinge or fold-line 4 is constructed so that it opposes opening of the portions 2 and 3 into a flat condition. This is achieved for the material of the invention when it is provided with the thickness previously indicated and with the formation of a shallow V-groove 16 for the formation of the hinge wherein the remaining thickness of the material at the groove 16 is a minor portion of the thickness of the material. As a consequence, there will be a natural bias built into the material tending to return it to a partially folded position whereby if the article lands face down, as shown in FIG. 3, there will be a space 17 formed beneath the article to allow circulation of air so that the adsorbed liquid can serve the deodorant function.

Although the invention has been described in relation to a specific embodiment thereof, it will be obvious to those skilled in the art that numerous modifications and variations can be made without departing from the scope and spirit of the invention. Thus, the grooves 11 and 12 which have been illustrated in both portions 2 and 3 of the sheet of the article could be formed as tongue and groove arrangements. Also, while both grid regions have been illustrated as being formed of crenalations, it is also possible to make one region depressed and the other region projecting.

Figure 4:
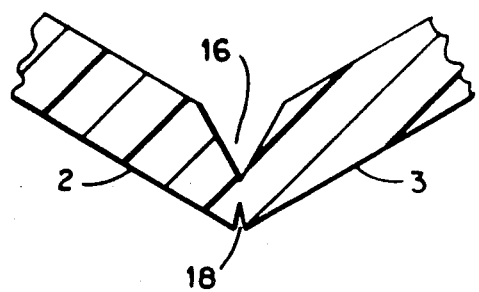
FIG. 4 is a view of a modified portion of the hinge of the article of FIGS. 1-3 on enlarged scale.

In order to insure that the article 1 will not be opened flat which could lead to blockage of the adsorbed liquid, other modifications could be used in replacement of the biassed hinge 4 of the described embodiment. For example, a stop could be built into the sheet to prevent its unfolding to flat condition as shown in FIG. 4 where the stop is formed of a narrow slit 18 in the back surface of the article below the groove 16.

Figure 5:
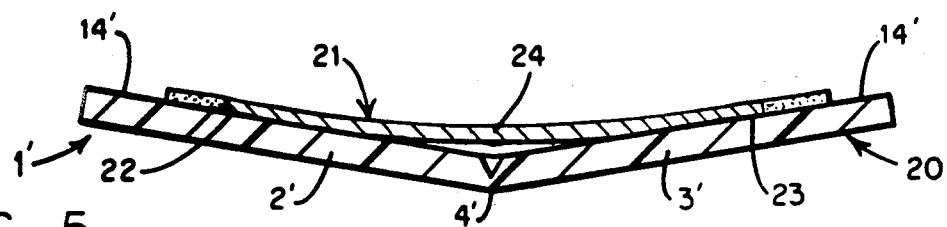
FIG. 5 is a sectional view of a modified embodiment of the article of the invention.
Figure 6:
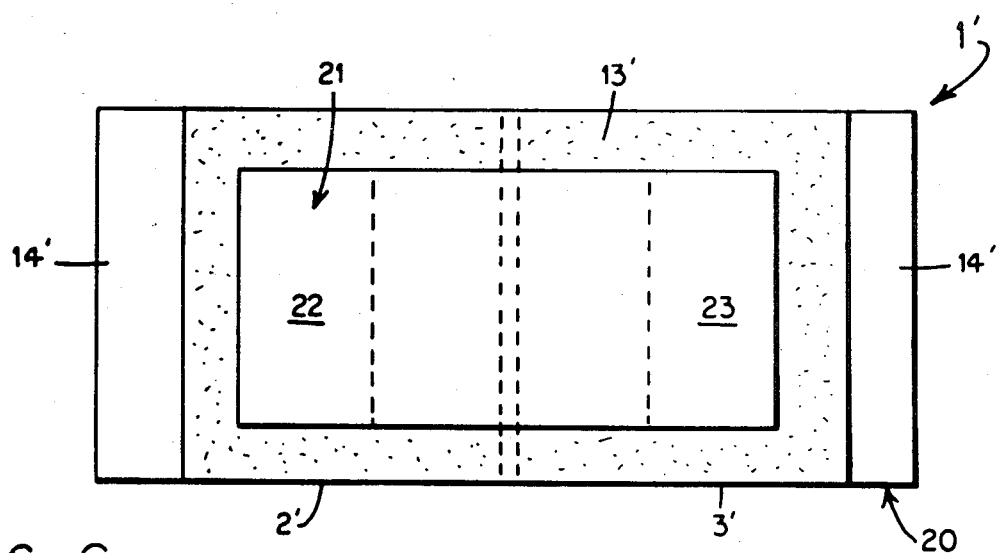
FIG. 6 is a plan view of the article of FIG. 5

In another modification illustrated in FIGS. 5 and 6, the article is designated by numeral 1' and is formed of two portions 2' and 3' hinged at 4'. The portions 2' and 3' are formed from a flat sheet 20 of plastic material such as PET and a peelable adhesive 13' is provided in the border region thereof in the manner illustrated in FIG. 6. However, instead of forming the grid regions with the adsorbed liquid therein as in FIG. 1, a separate sheet 21 of absorbent material such as porous paper is employed both for absorption of the deodorant liquid and as a means for preventing the sheet of plastic material from being folded into flat condition. Thus, as shown in FIGS. 5 and 6, the sheet 21 is affixed to the sheet 20 at spaced regions 22 and 23 and is unattached in region 24 such that the sheet 20 can only be opened to the partially unfolded state shown in FIG. 5, further opening of sheet 20 being resisted by sheet 21. The article 1' is used in the same manner as that of article 1 insofar that in the use article 1 is opened by grasping bare tabs 14' and unpeeling the portions along adhesive border 13 to expose the sheet 21 containing the absorbed deodorant. The article 1' is deposited into a toilet facility and if the facility contains water, the deodorant liquid will become dispersed therein in preparation for a deodorizing operation. As before, the article will be flushed away with the odorous material.

Figure 1:
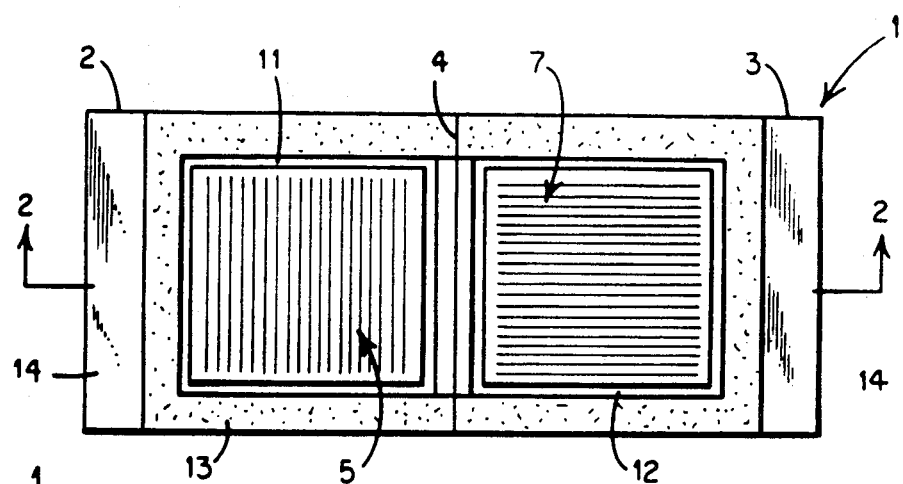
FIG. 1 is a plan view showing an embodiment of the article of the invention in opened state.
Figure 7:
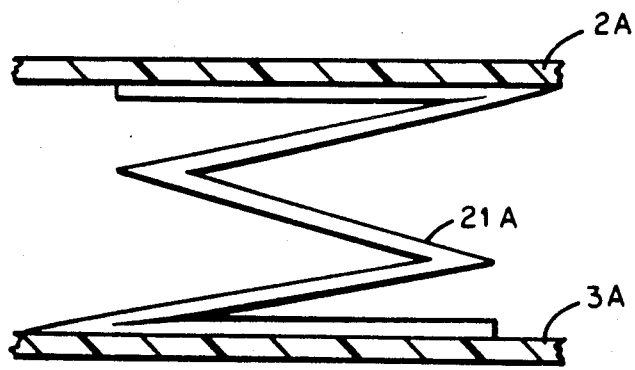
FIG. 7 is a sectional view of another modified embodiment of the article of the invention.

A modification is shown in FIG. 7 wherein instead of hinging portions together as in FIGS. 1 and 5, the portions are disconnected as shown at 2A and 3A and joined by a sheet 21A of absorbent material containing deodorant liquid. The sheet 21A is folded accordion style and the portions 2A and 3A are joined by peelable adhesive surrounding sheet 21A. In order to prepare the article for use, the portions 2A and 3A are separated by peeling the adhesive and the sheet 21A is unfolded by pulling the portions 2A and 3A away from one another.

The article is now ready for use in the manner previously described.

FIG. 8 shows an article 30 for dispensing the deodorant liquid in dropwise condition. The article 30 comprises a base 31 which includes a squeezable inner container 32 supported in an outer container 33, and a threaded closure cap 34 for the base 31.

As seen more particularly in FIG. 9, the inner container 32 is intended to store deodorant liquid 35 whose level when full is shown at 36. As liquid 35 is utilized, its level will drop within container 32. The deodorant liquid is of the type previously described and is generally a petroleum based, air-activated deodorant which floats on water and is dispersed as fine droplets when deposited thereon.

Accordingly, when deposited into a toilet facility containing water, the liquid deodorant will be exposed to the air and be effective to counteract odor by molecular interaction. In the event the toilet facility is a bed pan which does not contain water, the liquid will be directly exposed to the air.

An outlet or dispenser means 37 in the form of a sleeve nozzle is press-fit into a hole 38 at the top of inner container 32 in order to dispense the liquid 35 dropwise from the inner container 32 when the article 30 is inverted and the sleeve nozzle faces downwardly. The sleeve nozzle is provided with a calibrated bore 39 through which the liquid is constrained to flow in dropwise state when pressure is applied to the inner container 32.

The inner container 32 is preferably made from high-density polyethylene which has been fluorinated to provide barrier properties against transmission of odor of the liquid within the container.

The class of substances suitable for the inner container are fluoroplastics, such as polytetrafluoroethylene (PTFE), fluorinated ethylene propylene (FEP) copolymer, perfluoroalkoxy (PFA) resin, polychlorotrifluoroethylene (PCTFE), ethylene-chlorotrifluoroethylene (ECTFE) copolymer, ethylene-tetrafluoroethylene (ETFE) copolymer, polyvinyldene fluoride (PVDF), and polyvinylfluoride (PVF).

Instead of being made in entirety of a fluoroplastic, the inner container can be composed of a plastic body with a barrier layer of fluoroplastic applied to its inner surface.

The sleeve nozzle 36 can be made from relatively rigid high-density polypropylene.

The inner container 32 is sufficiently flexible so as to be squeezable so that by application of external force thereto, the liquid 35 can be discharged dropwise through calibrated bore 39 in the sleeve nozzle 37.

The outer container 33 which supports inner container 32 is more rigid than the inner container and it can be made from any suitable plastic material such as polypropylene, polyethylene, polyvinylidene or the like. The rigidity of the outer container 33 is such that application of pressure thereto by hand or by a fall will not produce a force on the inner container and cause discharge of liquid therefrom.

As seen in FIG. 10, a weighted plug 40 is threadably engaged in the bottom wall 41 of the outer container 33 and the plug 40 bears against a bottom wall 42 of the inner container 32. In this way, an upper shoulder 43 of container 32 can be pressed against the inner surface of a shoulder 44 of the outer container 33 so that the inner container 32 will be tightly and securely engaged within the outer container 33. A neck portion 45 of the inner container 32 is tightly fitted within an opening 46 in the shoulder 44 of the outer container 33.

The bottom 41 of the outer container 33 has feet 47 to enable the article 30 to stand on horizontal support surfaces. As an alternative, the bottom surface of bottom wall 41 of the outer container 33 can be made planar and formed with a non-skid surface. In order to keep the article upright on the support surface and prevent inadvertent tipping thereof, the plug 40 is weighted to lower the center of gravity of the article 30.

In order to enable the user to view the amount of liquid 35 within the inner container 32, the outer container 33 is provided with an opening in the form of a slot 48 extending along a length from the bottom 42 of the inner container to the location of the level 36 of the liquid when the inner container is filled. The inner container 32 is translucent at least at the slot 48 so that the user will be able to readily determine the amount of liquid remaining in the inner container 32. The outer container 33 is substantially greater in size than the inner container 32 for reasons to be explained later and the inner container is substantially cylindrical whereas the outer container is conical. The side walls of the inner and outer containers are spaced from one another to form a space 49 therebetween. For reasons also to be explained later, the side wall of the outer container 33 is preferably thickened locally as shown at 50 in FIG. 10 in order to bear against the outer surface of the inner container 32 around slot 48.

The slot 48 has an upper edge 51 which defines a ridge 52 above the slot and the outer container 33 is formed with slits 53 which extend from the edge 51 of the slot 48 to the lower edge of shoulder 44. In this way ridge 52 forms an actuator button which is effectively hinged at its upper edge to the shoulder 44 and which when pushed inwardly serves to apply pressure to the inner container 32 to effect dropwise discharge of the deodorant liquid when the base 31 is inverted.

In order to capture any overflow liquid that may run down the outer surface of sleeve nozzle 37 when the base is returned to its upright position after a discharge operation, the outer container 33 is formed with a reservoir constituted by an annular groove 54 which surrounds the neck portion 45 of the inner container 32. In general, as the liquid deodorant is volatile, it will accumulate in the reservoir 54 and evaporate. An absorbent material (not shown) can either form a lining for the reservoir 54 or completely fill the same. Additionally, a passage means in the form of grooves 55 can be provided in outer container 33 to establish communication between reservoir 54 and the space 49 between the containers so that any captured liquid can flow into this space. In order to prevent outflow of captured liquid through slot 48, the inner surface of the outer container is configured to bear against the outer surface of the inner container around the slot as previously described.

Figure 11:
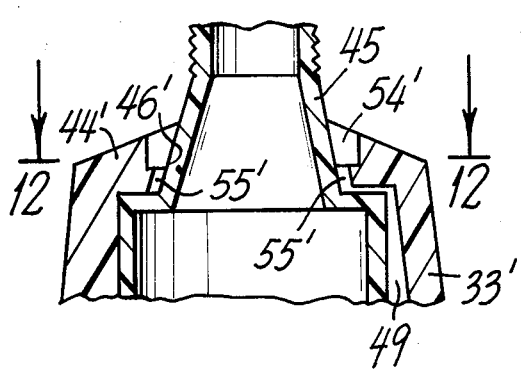
FIG. 11 is a sectional view of a part of a modified embodiment of the article.
Figure 12:
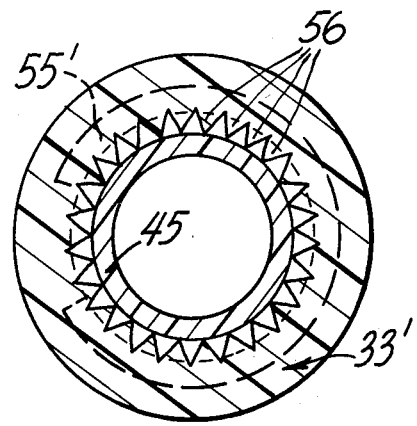
FIG. 12 is a sectional view taken on line 12—12 in FIG. 11.

FIGS. 11 and 12 show another embodiment for capturing the liquid. Those elements which are the same as in FIGS. 8-10 will be designated by the same reference characters and modified elements will be designated with primes. In FIGS. 11 and 12, it can be seen that the reservoir 54' is formed by a series of dentalations 56 in the inner surface of the shoulder 44' of the outer container 33'. When the neck portion 45 of the inner container 32 is press-fit in the opening 46' in the outer container formed by the dentalations 56, these will define the reservoir 54' into which the overflow liquid can be captured. As seen in FIG. 11, the dentalations 56 extend only partway through the depth of the shoulder 44' whereby overflow liquid can be stored in the reservoir 54' and allowed to evaporate into the atmosphere. Grooves 55' can be formed in the outer container 33' to establish communication between reservoir 54' and space 49.

Figure 14:
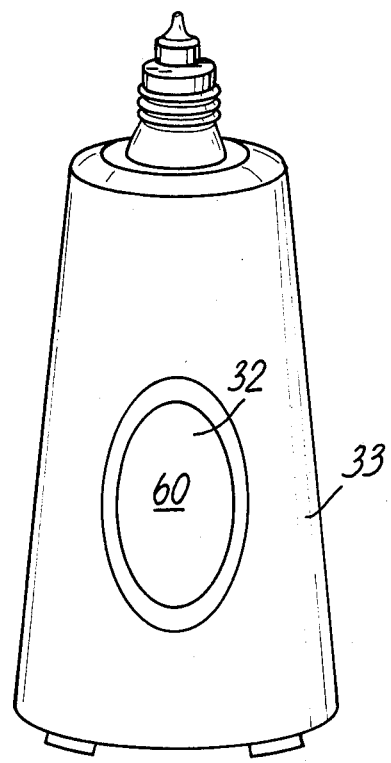
FIG. 14 is a view similar to FIG. 8 of a modified embodiment of the article.

FIG. 14 shows a modified embodiment in which the slot 48 has been replaced by an elongated opening 60 which serves the dual purpose of permitting the user's thumb to apply direct force to the inner container while serving as a window to reveal the level of the liquid in the inner container. In this way, the actuator button 52 in the embodiment in FIG. 8 is eliminated and the construction is simplified.

Figure 13:
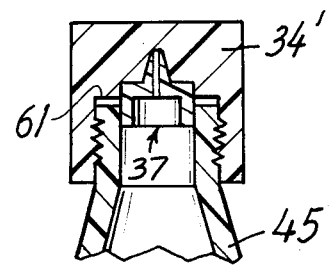
FIG. 13 is a sectional view showing a modified cap.

FIG. 13 shows a modified embodiment of the cap, designated by 34', which is constructed in order to minimize evaporation losses through bore 39. The cap 34' has an inner surface 61 which is shaped to conform to the outer surface of the sleeve nozzle 37 when the cap is fully screwed onto the neck portion 45 of the inner container. Thereby, the bore 39 in the sleeve nozzle 37 will be completely obturated when the cap is on the neck portion 45. This construction provides a double seal for the liquid in the inner container at the bore 39 and at the threads to minimize evaporation losses.

In assembly, the inner container 32 is inserted through the opening 57 in the bottom wall 41 of the outer container 33 until the shoulder 43 of the inner container abuts against the shoulder 44 of the outer container. The neck portion 45 will tightly extend through the opening 46 in the outer container. The weighted plug 40 is then threaded into the bottom 41 of the outer container 33 to force the shoulder 43 tightly against shoulder 44 and securely hold the inner container 32 within the outer container 33. The base 31 is now fully assembled and the cap 34 can be threaded onto neck portion 45 to complete the assembly of the article 30. The article 30 is now ready for use.

In use, the cap 34 is removed and the base 31 is inverted so that calibrated bore 39 in nozzle sleeve 37 faces downwardly. The actuator button 52 can then be pressed against the wall of the inner container 32 to apply pressure to the liquid content to force the liquid to be discharged from the bore 39 in droplet form.

As previously explained, it is intended that the liquid be discharged into the toilet facility prior to use as the liquid will act in a captive atmosphere and operate by molecular interaction to destroy subsequent malodor. If the liquid is dispensed into a toilet facility containing water, the liquid will break up into minute droplets which will be dispersed in floating relation on the surface of the water for air activation. When the contents of the toilet facility are flushed away, no lingering deodorant scent remains as would be the case with conventional sprays and slow-release liquids. After dispensing the liquid, the base 31 is returned to its upright position and the cap 34 is threaded onto the neck portion 45 of the inner container to close the article.

According to the concept of the invention, the article 30 is made of a size which discourages portability and which is intended for being stably supported in upright state on a support surface by virtue of the weighted plug 40. The weighted plug not only opposes tipping of the article, but also discourages its portable use in one's pocket or in a pocketbook.

The outer container 33 has a slightly conical shape and is of much greater size than the inner container so as to provide a handling surface which can be adapted to the normal size of the hand of a user. The sloping surface also prevents the article from slipping when the outer container is held in inverted condition for use in dispensing liquid droplets. In general, the support of the inner container at its upper and lower ends between the shoulder 44 of the outer container and plug 40 permits the formation of the space 49 between the side walls of the inner and outer containers which effectively prevents any undesired discharge of liquid if the article is dropped. Also inadvertent application of squeezing pressure to the outer container, will not cause discharge of liquid.

After the liquid content in the inner container has been exhausted, as verified through the slot 48 in the outer container of FIG. 8 or the opening 60 in the outer container of FIG. 14, the plug 40 can be unscrewed from the bottom 41 of the outer container to remove the now empty inner container 32. A fresh inner container is secured in place by screwing the plug 40 into the bottom of the outer container. If no replacement of the inner container is contemplated, for example, for simplification of construction and economy in production, instead of threaded plug 40, a weighted plug can be press-fit in the bottom of the outer container. Consequently, when the liquid in the inner container is exhausted, the entire article is thrown away.

The concept of the invention of the dropwise addition of the liquid deodorant to counteract malodor of fecal matter is to be distinguished from conventional airborne sprays and wicks which leave prolonged cover-up odors which themselves can be offensive. The invention falls into that category of treatment in which molecularly interactive liquids are employed for odor absorption. Such liquids are not suitable for spraying as they are naturally objectionable in odor. Liquids which are water-soluble have been added into a toilet facility to provide a fecal bath or to produce a foaming action to smother fecal matter. This is an after treatment and is in contrast with the invention where the liquid addition is effected prior to use to create a captive atmosphere in the toilet facility which will neutralize malodor. The deodorant liquid employed in the invention is effective for its purposes as it is oil or petroleum based, air-activated, dispersible on water in minute droplet form and molecularly interacts in the air to negate fecal malodor.

In addition, the article of the invention provides the user with a means of accurate measurement to dispense, in droplet form, only so much deodorizer as is needed. This avoids any offensive odors associated with excessive quantities of the deodorant liquid.

As the product will probably be used in a hard-surfaced environment such as a bathroom whose floors and walls are made from ceramic tile and the fixtures from vitreous china, a container of glass is undesirable since, if accidentally dropped it would almost certainly break, causing shards of glass to fly and the liquid contents to splash. The user would be in danger not only of being cut but also of being exposed to an obnoxious substance. Additionally, glass is rigid and cannot be squeezed to produce a force to expel the contents in the container. The plastic article of the invention has the advantages of being both unbreakable and squeezable. Moreover, the plastic article is inert to the deodorant liquid and non-permeable to the odor of the liquid deodorant.

The fluorination of the high density polyethylene inner container satisfies these requirements. Hence, the article of the invention is comprised of four parts:

1. High-density polyethylene container 32 of cylindrical shape with semi-rigid walls and extended threaded neck portion 45.

2. Polyethylene sleeve nozzle 37 which is press-fit in the neck portion 45 to form a tight seal. The sleeve nozzle 37 has a conical tip with droplet-forming bore 39 for the discharge of one drop at a time only when external force is applied to the container 32. The shape and rigidity of container 32 acts to prevent unintentional discharge and does not allow sufficient pressure to be exerted to cause liquid to be discharged as a steady stream or spray. The sleeve nozzle need not be fluorinated.

3. Polypropylene cap 33 which forms a sealed closure with the neck portion 45 and in the embodiment of FIG. 13 an internal shape conforming precisely with the shape of the sleeve nozzle to provide a tight seal which prevents any seepage from the bore 39.

4. Outer container 32 which projects inner container 31 and is more rigid than the inner container. The container 32 can absorb shocks from dropping without causing any discharge of liquid from the protected inner container 31.

What is claimed is:

1. Apparatus for dispensing a deodorant liquid dropwise comprising an article including an inner container for a deodorant liquid which is floatable on water in dispersed droplet form, said inner container having an outlet means for dispensing of said liquid therefrom, and an outer container supporting and enclosing said inner container therein with said outlet means outside said outer container, said outer container including means through which the inner container and the liquid therein are visible and actuator means associated with said outer container for the application of actuating force via said outer container to said inner container to cause discharge of liquid dropwise through the outlet means thereof with the article inverted and said outlet means facing downwardly.

2. Apparatus as claimed in claim 1 wherein said actuator means is on said outer container in the vicinity of said opening.

3. Apparatus as claimed in claim 2 comprising weight means on said outer container for holding the article in upright position.

4. Apparatus as claimed in claim 3 wherein said inner container is replaceable in said outer container.

5. Apparatus as claimed in claim 4 wherein said outer container has a closable aperture, said inner container being insertable into and removable from said container through said aperture, said outer container including a removable plug for closing said aperture.

6. Apparatus as claimed in claim 1 wherein said outer container includes a shoulder against which said inner container is in abutment.

7. Apparatus as claimed in claim 6 wherein said outlet means of the inner container projects through said shoulder, said shoulder having an outer surface with means for capturing any overflow liquid from said outlet means.

8. Apparatus as claimed in claim 7 wherein said inner and outer containers form passage means for flow of captured liquid into the outer container.

9. Apparatus as claimed in claim 8 wherein said means of the outer container through which the inner container is visible incorporates a slot which forms a ridge thereabove beneath said shoulder, said ridge having an inner surface bearing against said inner container, said ridge being provided with spaced slits to form an actuator button, said actuator means comprising said actuator button.

10. Apparatus as claimed in claim 9 wherein said means for capturing any overflow liquid comprises spaced dentalations on one of said containers, extending partially along the length thereof.

11. Apparatus as claimed in claim 1 wherein said means of the outer container through which the inner container is visible includes a portion having an opening in the outer container dimensioned to permit a user to insert the user's thumb in said opening to apply direct pressure to said inner container, the aforesaid dimensioned opening provided said actuator means by which the actuating force can be applied to the inner container.

12. Apparatus as claimed in claim 1 wherein said outlet means includes a projection with a bore therein, said apparatus further comprising a cap removably affixable to said outlet means and having an inner surface which is shaped to conform to said projection to close said bore when the cap is affixed to the outlet means.

13. A method of neutralizing odor of human evacuation into a toilet facility comprising storing an odor-neutralizing liquid in an inner container, supporting said inner container in an outer container, providing an outlet for said inner container, supporting and enclosing the inner container within the outer container so that the outlet of the inner container opens externally of the outer container, forming said outlet so that application of external force to the inner container will produce dropwise discharge of the odor-neutralizing liquid when the outer container is held in an inverted position in which the outlet of the inner container faces downwardly, providing a window in the outer container through which the liquid contents in the inner container are visible, and depositing drops of said odor-neutralizing liquid into said toilet facility by application of external force to the inverted inner container via said container.

14. A method as claimed in claim 13 wherein the external force is applied to the inner container through application of force to the outer container.

15. A method as claimed in claim 13 wherein said drops of the odor-neutralizing liquid are introduced into the toilet facility prior to evacuation thereinto.

16. A method as claimed in claim 13 wherein said odor-neutralizing liquid is an oil-based, air-actuated liquid which floats on water in dispersed droplet form.

17. A method as claimed in claim 13 comprising capturing any overflow liquid from the outlet of the inner container in a reservoir in the outer container.

18. A method as claimed in claim 17 comprising conveying the overflow liquid into the interior of the outer container.

19. A method as claimed in claim 13 comprising replacing the inner container in the outer container with another filled inner container after the liquid in the first inner container is spent.

* * * * *